United States Patent [19]

Rothschild

[11] Patent Number: 5,642,394
[45] Date of Patent: Jun. 24, 1997

[54] SIDESCATTER X-RAY DETECTION SYSTEM

[75] Inventor: Peter John Rothschild, Cambridge, Mass.

[73] Assignee: American Science and Engineering, Inc., Billerica, Mass.

[21] Appl. No.: 627,007

[22] Filed: Apr. 3, 1996

[51] Int. Cl.[6] .................................................. G01N 23/04
[52] U.S. Cl. .............................. 378/57; 378/86; 378/87
[58] Field of Search ............................ 378/51, 53, 57, 378/86, 87, 88, 62

[56] References Cited

U.S. PATENT DOCUMENTS

| Re. 28,544 | 9/1975 | Stein et al. | 250/369 |
|---|---|---|---|
| 2,670,401 | 2/1954 | Weinberg | 178/6.8 |
| 4,357,535 | 11/1982 | Haas | 378/57 |
| 4,799,247 | 1/1989 | Annis et al. | 378/87 |
| 4,884,289 | 11/1989 | Glockmann et al. | 378/57 |
| 5,181,234 | 1/1993 | Smith | 378/87 |
| 5,260,982 | 11/1993 | Fujii et al. | 378/87 |
| 5,313,511 | 5/1994 | Annis et al. | 378/87 |
| 5,420,905 | 5/1995 | Bertozzi | 378/88 |

OTHER PUBLICATIONS

G. Harding, "On the Sensitivity and Application Possibilities of a Novel Compton Scatter Imaging System", *IEEE Transactions on Nuclear Science*, vol. NS-29, No. 3, Jun. 1982, pp. 1260–1265.

E.E. Murphy, "A Rising War on Terrorists", *IEEE Spectrum*, Nov. 1989, pp. 33–36.

J.A. Stein and R.D. Swift, "Flying Spot X-Ray Imaging Systems", American Science and Engineering, Inc., ASE-2864, Dec. 1971, pp. i–17.

J.A. Stein and R.D. Swift, "Flying Spot X-Ray Imaging Systems", *Materials Evaluation*, American Society of Nondestructive Testing, vol. XXX, No. 7, Jul. 1972, pp. 137–148.

J.A. Stein, "X-Ray Imaging with a Scanning Beam", *Radiology*, vol. 117, Dec. 1975, pp. 713–716.

B.C. Towe and A.M. Jacobs, "X-Ray Compton Scatter Imaging Using a High Speed Flying Spot X-Ray Tube", *IEEE Transactions on Biomedical Engineering*, vol. BME-28, No. 10, Oct. 1981, pp. 717–721.

E.J. Tracy, "A New X-Ray Scanner to Hinder Hijackers", *Fortune*, Apr. 28, 1986, p. 146.

*Primary Examiner*—Don Wong
*Attorney, Agent, or Firm*—Pollock, Vande Sande & Priddy

[57] ABSTRACT

An edge enhancement X-ray imaging system inspects an object for detecting an illegal component. The system illuminates the object with penetrating radiation which is sidescattered from the object and captured by a pair of radiant detectors. The detectors are symmetrically positioned opposite each other, being adjacent the two sides of the object. Each detector has a detecting surface substantially parallel to the beam for converting sidescattered radiation into a pair of electrical signals which define a location of an edge of the illegal component. In response to the electrical signals, a video display produces a visual image of the edge. In another embodiment of the invention, the system further comprises a pair of backscatter detectors which convert the backscattered radiation into a second pair of electrical signals producing a second visual image on the video display. As a result of superimposing the second image onto the first image associated with the sidescatter detectors, the detection of components of the object is greatly improved.

10 Claims, 2 Drawing Sheets

SIDESCATTER X-RAY DETECTION SYSTEM

FIELD OF THE INVENTION

This invention relates to radiant energy imaging systems and, in particular, systems for detecting the edges of low and high Z components, such as plastics, ceramics, metal, etc., during an inspection of an object.

BACKGROUND OF THE INVENTION

Lately, x-radiation has been extensively used in the security field for inspecting objects in airports, courthouses, federal buildings, etc. Various systems have been proposed to insure adequate resolution of an image at a relatively low intensity of radiation. For example, U.S. Pat. No. RE 28,544 to Stein et al describes an X-ray source generating radiation which is collimated to form a flying pencil beam for scanning a line in space. An object to be scanned is positioned in front of the X-ray source. An X-ray detector is then positioned farther away from the X-ray source than the object and directly behind the object at the line in space. After the X-ray source is turned on, the incident photons are converted by the detector into electrical signals which drive a video display. If the object to be inspected is translated in a direction transverse to the scanning line, the object can be fully scanned in the X–Y plane. This so-called forward transmitted detector can only detect those X-rays which are transmitted through the object without substantially changing their direction. Some X-rays do not reach the detector because they are absorbed by a component in the object. This results in a shadow which appears on the video display as an outline of that X-ray absorbing component.

The described use of X-ray illumination and imaging has proved particularly effective in detecting relatively dense, solid materials, such as conventional metal weapons, etc. Having a high atomic number (high Z), these dense materials absorb X-rays and produce an easily identifiable image displaying a shape of an illegal article. A security officer can then readily recognize certain distinct shapes, i.e., a handgun, etc., based on the video image.

Complications with detection, however, arise with materials having a low atomic number (low Z), such as plastic weapons, drugs, etc. These objects do not absorb but scatter X-rays producing fuzzy, vague and practically unrecognizable images of components made of low Z materials. Having this attribute, plastic or ceramic illegal objects are quite difficult to detect during inspections even by trained professionals.

Since low Z materials fail to produce clear, easily recognizable images using conventional techniques of the forward transmitted detector which only captures penetrating x-rays, various methods and systems have been proposed to solve the problem of detecting these materials using X-ray scanning and imaging. U.S. Pat. Nos. 4,799,247 and 5,313,511, both to Armis et al, and U.S. Pat. No. 5,181,234 to Smith illustrate systems for detecting, inter alia, backscatter radiation from low Z materials. These patents disclose systems for illuminating low Z materials and capturing the backscattered or reflected radiation onto a photosensitive detector. In contrast to the conventional technique of placing the detector behind an object to be illuminated by an X-ray source, the backscatter detector is positioned on the same side of the illuminated object as the X-ray source. The backscatter detector then provides an electrical signal representative of the intensity of the X-rays scattered from the object being scanned. Based on the electrical signal, an image of the object is shown on a video display for visual detection and identification of illegal materials.

An important property of any X-ray image is contrast. For example, when one low Z object appears in an image on top of another low Z object, such as the human body, the contrast between these two objects can be low. Similarly, a high Z object viewed against the background of another high Z object will also display low contrast. Consequently, the objects in the X-ray image appear as indistinct, without well defined outlines or edges.

Therefore, to significantly improve inspection of objects, either animate or inanimate, as disclosed by the prior art, the present invention is provided for enhanced edge detection and enhancement of materials using X-ray illumination and imaging.

SUMMARY OF THE INVENTION

The present invention includes an edge enhancement X-ray imaging system for inspecting an object to detect the edges of a component located on the object. The system comprises a source of penetrating radiation, means for forming radiation emitted by the source into a beam of predetermined cross-section, means for scanning the beam across the object to be inspected and a first pair of radiant detectors responsive to radiation sidescattered by the object. The detectors are symmetrically positioned opposite each other, being adjacent the two sides of the object. Each detector has an effective detecting surface substantially parallel to the beam for converting sidescattered radiation into a first pair of electrical signals. The difference in magnitude between the pair of electrical signals as a function of beam position provides information defining the location of edges of the component contained by the object.

Further in accordance with the present invention, a video display, driven by a processor, produces a visual image which includes a representation of the edges.

In accordance with another embodiment of the present invention, the system further comprises a second pair of detectors located closer to the source than the first pair of detectors and having an effective detecting surface substantially perpendicular to the scanning beam. Responding to the radiation backscattered by the object, the second pair of detectors converts the backscattered radiation into a second pair of electrical signals. This second pair of electrical signals accentuates the component of the object and produces a second visual image on the video display. When combined with the first image associated with the first pair of detectors, the second image further aids the detection of components contained within or on the inspected object.

BRIEF DESCRIPTION OF THE DRAWINGS

The above-mentioned as well as additional features of the present invention will be evident and more clearly understood when considered in conjunction with the accompanying drawings, in which.

In all Figures, like reference numerals represent same or identical components of the present invention.

DESCRIPTION OF THE PREFERRED EMBODIMENTS

Figure 1:
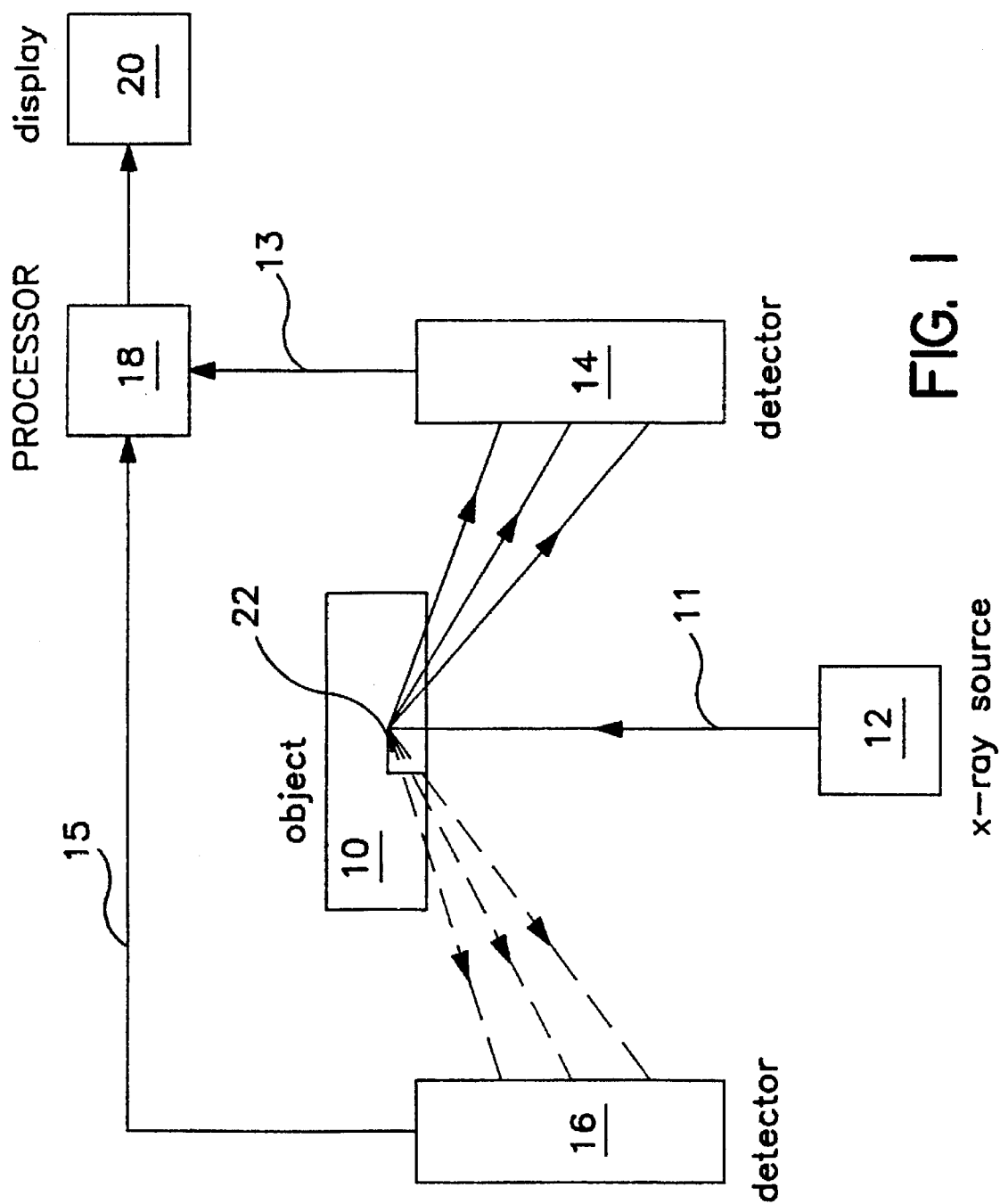
FIG. 1 shows a block diagram depicting a top view of an edge enhancement X-ray imaging system for inspecting an object.

FIG. 1 shows a block diagram depicting a top view of an edge enhancement X-ray imaging system for inspecting an object. FIG. 1 illustrates an object 10 (animate or inanimate) being inspected for detection of any illegal materials, such as an illegal low Z component 22. An X-ray source 12 generates radiation which is collimated to form a flying pencil beam 11 as disclosed by the previously mentioned Stein and/or Annis patents. The X-ray source 12 may scan the object 10 at a line in space in either horizontal or vertical direction depending on the arrangement of collimating slits. A full scan of the X–Y plane is achieved by translating either the object 10 or the X-ray source 12 in a direction transverse to the line in space.

Further shown in FIG. 1 are two radiant energy detectors 14 and 16 for capturing and converting the incident photons into electrical signals. The detectors 14 and 16 form a pair of detectors which are symmetrically positioned opposite each other adjacent two sides of the object 10 and located generally closer to the X-ray source 12 than the object 10. Each detector 14, 16 has an effective detecting surface substantially parallel to the flying pencil beam 11 and is positioned substantially outside a cross sectional area of the object 10 scanned by the flying pencil beam 11.

In accordance with FIG. 1, a processor 18 is connected to the detectors 14 and 16 via wires 13 and 15. The processor 18 responds to the electrical signals in the wires 13 and 15 by calculating a difference in magnitude between the electrical signals. This difference in magnitude between the two signals generated by the detectors 14 and 16 determines a location of an edge of the exemplary "illegal" low Z component 22 as will be more fully explained below. A video display 20, connected to the processor 18, produces a visual image which includes a representation of the edge of the illegal component 22.

Figure 2:
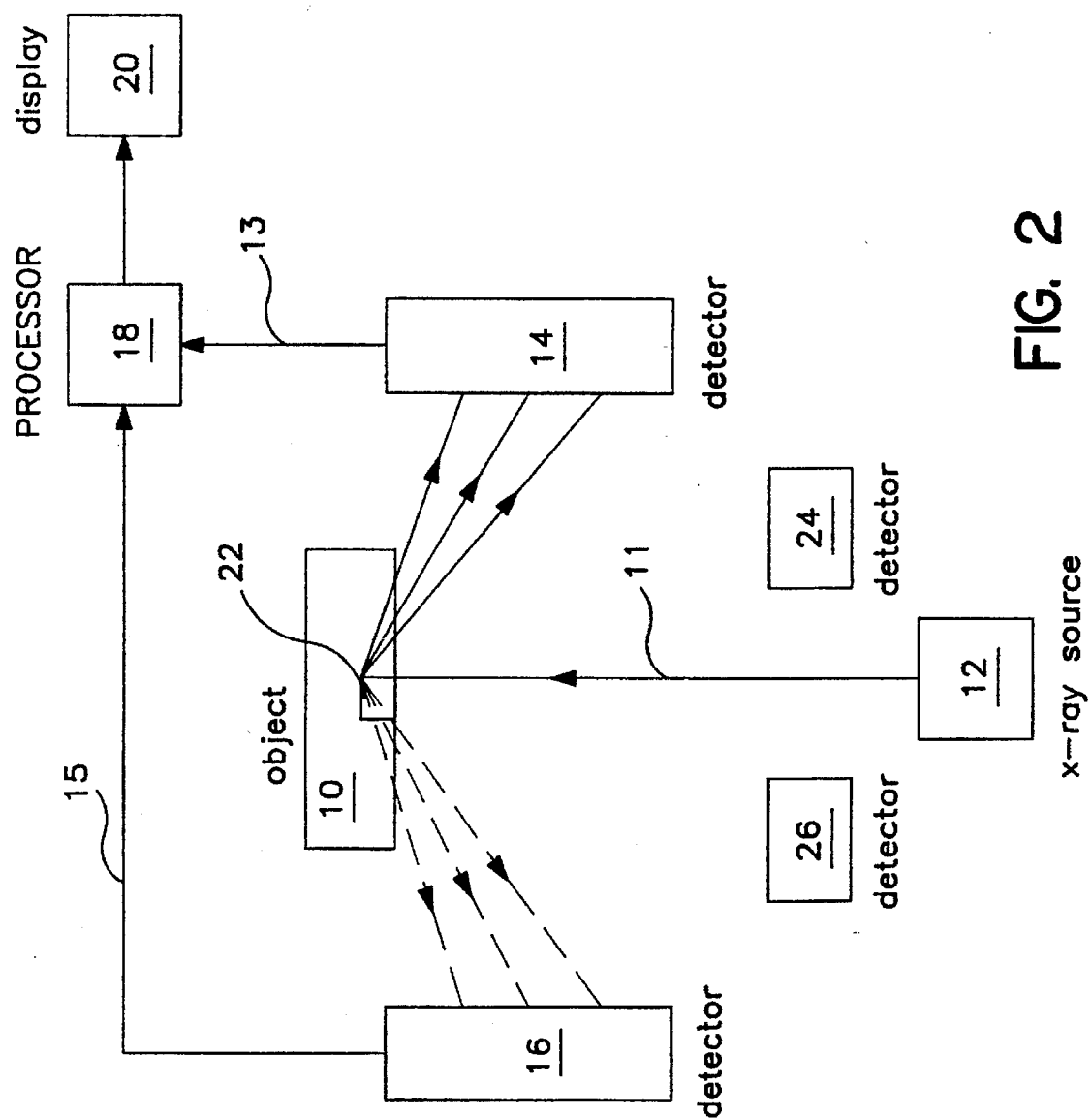
FIG. 2 shows a block diagram depicting a top view of another embodiment of the present invention comprising sidescatter and backscatter detectors for enhanced detection of components.

According to this embodiment of the present invention, inspection of the object 10 to detect the low Z component 22 proceeds as follows. Starting, for example, from the right side of the object 10, the flying pencil beam 11 of penetrating radiation scans across the object 10 which is moving transversely relative to the scanning beam 11 to obtain a full scan in the X–Y plane. Since FIGS. 1 and 2 show top views of the present invention, the X–Y plane is perpendicular to the plane of the drawing sheet and parallel to the object 10. Upon receiving radiation from the X-ray source 12, the object 10 will sidescatter X-rays to the sides. The X-rays will be sidescattered in substantially the same quantity or intensity to the two sides and about equally detected by the symmetrically positioned radiant detectors 14 and 16. Electrical signals, generated by the detectors 14 and 16, will not significantly differ in magnitude as calculated by processing means within the processor 18. Responding to an output signals from the processor 18, the corresponding video display 20 will not have any display due to the absence of or insignificant difference between the two electrical signals.

As the scanning proceeds to the left of the object 10, the difference in magnitude between the two electrical signals will start increasing gradually as a result of the attenuation of photons reaching the detector 16, as shown in FIG. 1. The path of the photons sidescattered from the object 10 will be increasingly blocked by the low Z component 22 as the flying pencil beam 11 scans across the object 10 in the direction of the illegal low Z component 22. Thus, in contrast to the unattenuated sidescattered radiation emitted from the right side of the object 10, the reduced photon detection is encountered as the illegal low Z component 22 is approached. This is due to a partial absorption and additional scatter of X-rays by the illegal low Z component 22, as shown by the dash lines in FIG. 1. The difference in magnitude increases between the two electrical signals generated by the detectors 14 and 16, until the maximum difference is reached at the edge of the illegal low Z component 22. The detector 14 detecting larger quantity of X-rays than the detector 16 will correspondingly produce a larger electrical signal, as calculated by the processor 18 and continuously shown on the video display 20. When the difference in magnitude between the two signals reaches the largest value, the video display 20 will produce an easily identifiable, clear representation of the edge of the illegal low Z component 22.

It is understood that the low Z component was only used for illustrative purposes in the above description. The present invention will equally enhance the detection of edges of high Z components, such as iron or aluminum, located on the background object formed either of a high Z or low Z material.

In accordance with another aspect of the present invention, a computer storage, which may be located in the processor 18, stores atomic numbers of various components in correspondence with the difference in magnitude between the two electrical signals in the pair. The atomic numbers and the magnitude differences may be arranged in a look-up table, for example. After calculating the magnitude difference between the two signals, the processor 18 will access the table in order to determine an approximate atomic number of the component being viewed.

For example, at low energy levels of approximately 15 KeV, a difference in magnitude is approximately 22% for plastic or ceramic components between the two detectors 14, 16 when the beam is illuminating the edge of the component. For aluminum and iron, at 15 KeV, the differential magnitude is approximately 75% between the two detectors 14, 16. Thus, upon calculating the difference in magnitude between the two signals, the processor 18 accesses the look-up table for determining an approximate atomic number of the component. The magnitude difference of 50% or lower will indicate that the component is a substantially low Z component, while the higher magnitude difference will signify a substantially high Z component.

In another embodiment of the present invention, FIG. 2 shows a block diagram of a top view of an X-ray imaging system with sidescatter and backscatter detectors for inspecting the object 10 to detect the illegal low Z component 22. The system in FIG. 2, having the same arrangement as in FIG. 1, i.e., the detectors 14 and 16, the X-ray source 12, the processor 18 and the video display 20, includes an additional pair of radiant detectors 24 and 26.

This second pair of detectors 24, 26 is located closer to the X-ray source 12 than the first pair of detectors 14, 16. The detectors 24 and 26 have an effective detecting surface substantially perpendicular to the flying pencil beam 11 and are responsive to radiation backscattered by the object 10.

Next, operation of the system shown in FIG. 2 will be described. The object 10 will both sidescatter and backscatter X-rays as the flying pencil beam 11 scans across the object 10. The sidescattered X-rays will be detected by the symmetrically positioned detectors 14 and 16 as explained above with reference to FIG. 1. The backscattered X-rays will be detected by the detectors 24 and 26 arranged for capturing the backscattered radiation.

As the scanning proceeds toward the illegal low Z component 22, the difference in magnitude will increase between the two electrical signals generated by the detectors 14 and 16, as calculated by the processor 18 and continuously shown on the video display 20, in accordance with the above description. According to the technique known in the prior art, the backscatter radiation will also be continuously detected by the detectors 24 and 26 and converted into a second pair of electrical signals which represent the illegal low Z component 22. The second visual image is continuously displayed on the video display 20. The two images are then superimposed on each other on the video display 20. This provides an overall enhanced detection capability of the illegal low Z component 22.

Since those skilled in the art can modify the disclosed specific embodiment without departing from the spirit of the invention, it is, therefore, intended that the claims be interpreted to cover such modifications and equivalents.

What is claimed is:

1. An edge enhancement X-ray imaging system for inspecting an object, comprising:

a source of penetrating radiation;

means for forming radiation emitted by said source into a beam of predetermined cross-section;

means for scanning said beam across said object to be inspected;

responsive to radiation sidescattered by said object, a first pair of radiant detectors symmetrically positioned opposite each other and being adjacent two sides of said object for converting sidescattered radiation into a first pair of electrical signals including information defining a location of an edge of a component of said object;

processing means responsive to said first pair of electrical signals for determining a difference in magnitude therebetween, said difference being dependent on a position of said beam during the scanning of said object; and display means responsive to said processing means for producing a first visual image which includes a representation of said edge of a component located on said object.

2. The system according to claim 1, further comprising storage means for storing information representative of atomic numbers of components in correspondence with said difference in magnitude, wherein said processing means access said storage means for determining an approximate atomic number of said component based on said difference in magnitude between electrical signals of said first pair.

3. The system according to claim 1, wherein each detector of said first pair of radiant detectors has an effective detecting surface substantially parallel to said beam.

4. The system according to claim 1, wherein said processing means include means for calculating said difference in magnitude between electrical signals in said first pair of electrical signals.

5. The system according to claim 1, further comprising a second pair of detectors located closer to said source than said first pair of detectors, said second pair of detectors having an effective detecting surface substantially perpendicular to said beam and being responsive to radiation backscattered by said object, wherein said second pair of detectors converts said backscattered radiation into a second pair of electrical signals including information for generating a second visual image superimposed onto said first visual image on said display means, thereby providing an enhanced detection of said component.

6. The system according to claim 1, wherein each detector of said first pair of detectors is positioned substantially outside a cross sectional area of said object scanned by said beam.

7. A method of inspecting an object using an edge enhancement X-ray imaging system, said method comprising the steps of:

scanning a beam of penetrating radiation across said object;

moving said object relative to said scanning beam;

detecting radiation sidescattered by said object;

converting sidescattered radiation into a first pair of electrical signals which include information defining a location of an edge of a component of said object;

determining a difference in magnitude between electrical signals of said first pair, said difference being dependent on a position of said beam during the scanning of said object; and producing a first visual image of said edge in response to said determination.

8. The method according to claim 7, wherein said determination comprises calculating a difference in magnitude between electrical signals of said first pair of electrical signals.

9. The method according to claim 7, further comprising:

detecting radiation backscattered by said object;

converting said backscattered radiation into a second pair of electrical signals representative of said component;

producing a second visual image of said component in response to said conversion; and superimposing said second visual image onto said first visual image to provide an enhanced detection of said component.

10. The method according to claim 7, further comprising:

providing storage means for storing information representative of atomic numbers of components in correspondence with said difference in magnitude;

accessing said storage means; and determining an approximate atomic number of said component based on said difference in magnitude between electrical signals of said first pair.

* * * * *